United States Patent [19]

Klawitter

[11] 4,373,216
[45] Feb. 15, 1983

[54] HEART VALVES HAVING EDGE-GUIDED OCCLUDERS

[75] Inventor: Jerome J. Klawitter, Austin, Tex.

[73] Assignee: Hemex, Inc., Austin, Tex.

[21] Appl. No.: 302,693

[22] Filed: Sep. 15, 1981

Related U.S. Application Data

[63] Continuation-in-part of Ser. No. 200,910, Oct. 27, 1980, abandoned.

[51] Int. Cl.³ .............................................. A61F 1/22
[52] U.S. Cl. ........................................ 3/1.5; 137/512.1; 137/527; 137/527.8
[58] Field of Search ............... 3/1.5; 137/512.1, 527, 137/527.8

[56] References Cited

U.S. PATENT DOCUMENTS

| | | | |
|---|---|---|---|
| 3,476,143 | 11/1969 | Kaster | 3/1.5 X |
| 3,825,957 | 7/1974 | Kaster | 3/1.5 |
| 3,835,475 | 9/1974 | Child | 3/1.5 |
| 4,078,268 | 3/1978 | Possis | 3/1.5 |
| 4,123,805 | 11/1978 | Kramer et al. | 3/1.5 |
| 4,159,543 | 7/1979 | Carpentier | 3/1.5 |
| 4,178,638 | 12/1979 | Meyer | 3/1.5 |
| 4,178,639 | 12/1979 | Bokros | 3/1.5 |
| 4,225,980 | 10/1980 | Martinez | 3/1.5 |
| 4,240,161 | 12/1980 | Huffstutler et al. | 3/1.5 |
| 4,263,680 | 4/1981 | Reul et al. | 3/1.5 |
| 4,272,854 | 1/1981 | Bokros | 3/1.5 |
| 4,276,658 | 7/1981 | Hanson et al. | 3/1.5 |

Primary Examiner—Ronald L. Frinks
Attorney, Agent, or Firm—Fitch, Even, Tabin, Flannery & Welsh

[57] ABSTRACT

Heart valves having valve members which are guided between their open and closed positions by projections extending inward from the annular body and interengaging with complementary notches in the peripheries of the occluders. Protuberances associated with the projections cooperate to define the pivotal axes, serve as open and closed position stops, and retain the valve members within the valve body.

25 Claims, 21 Drawing Figures

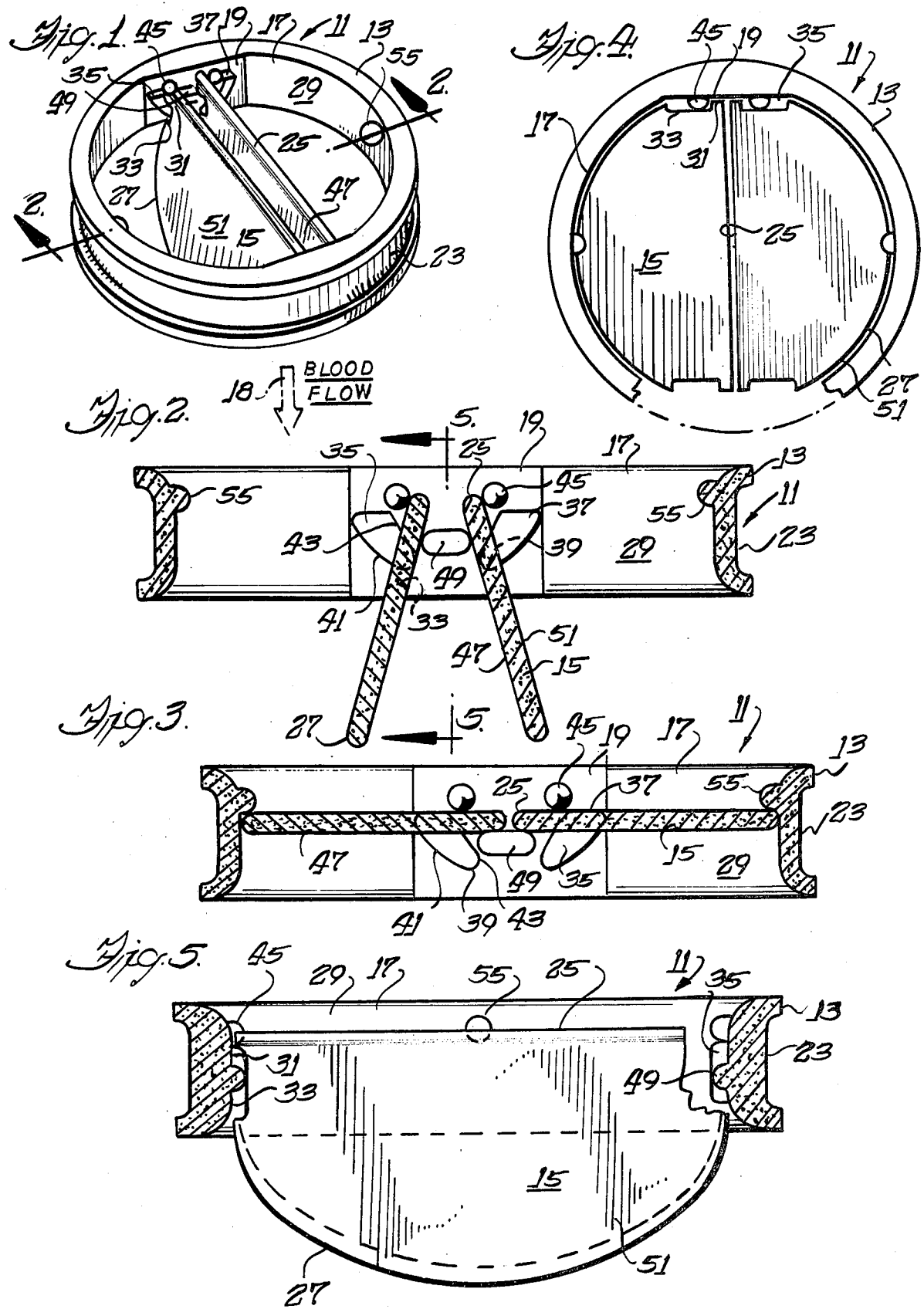

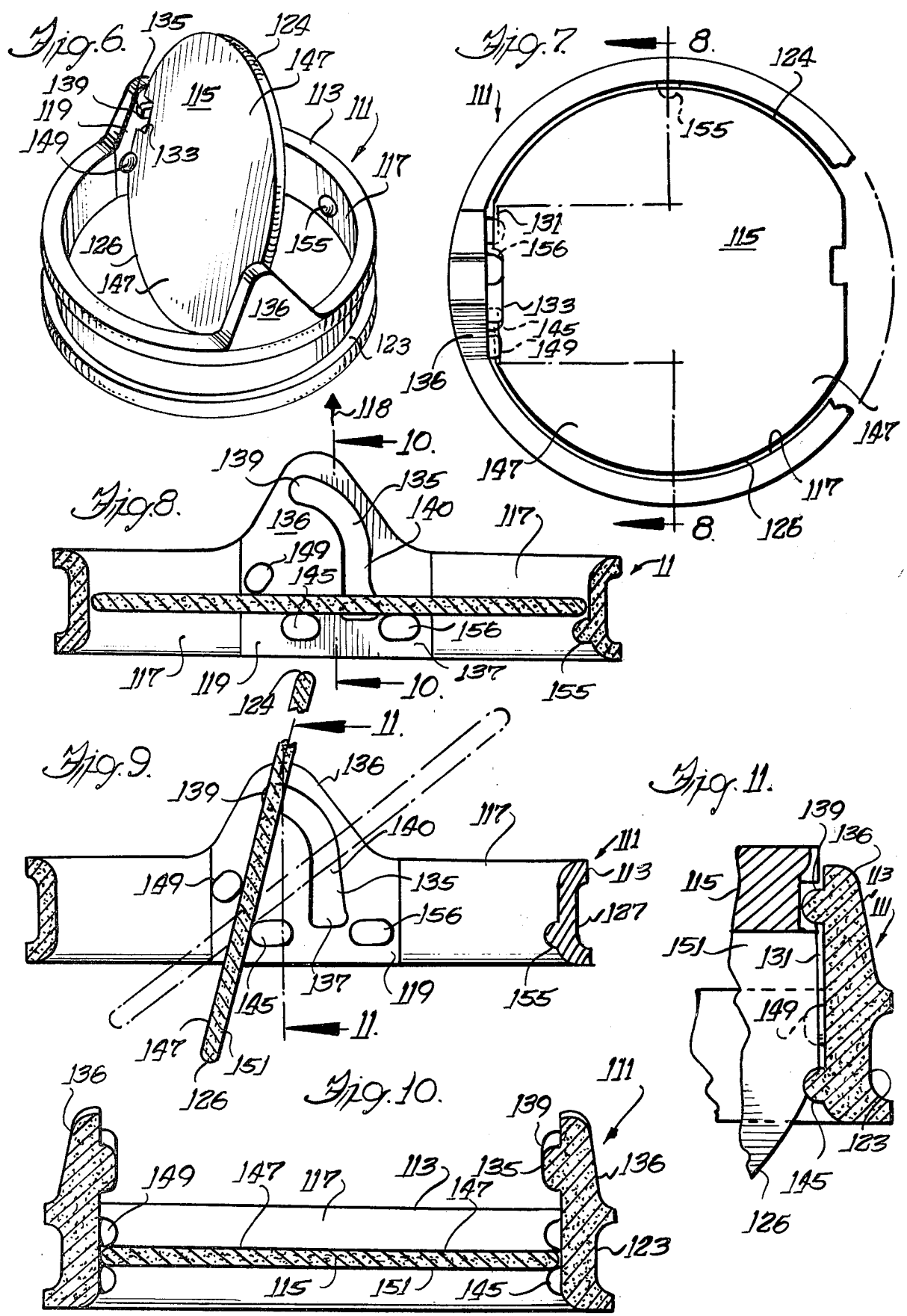

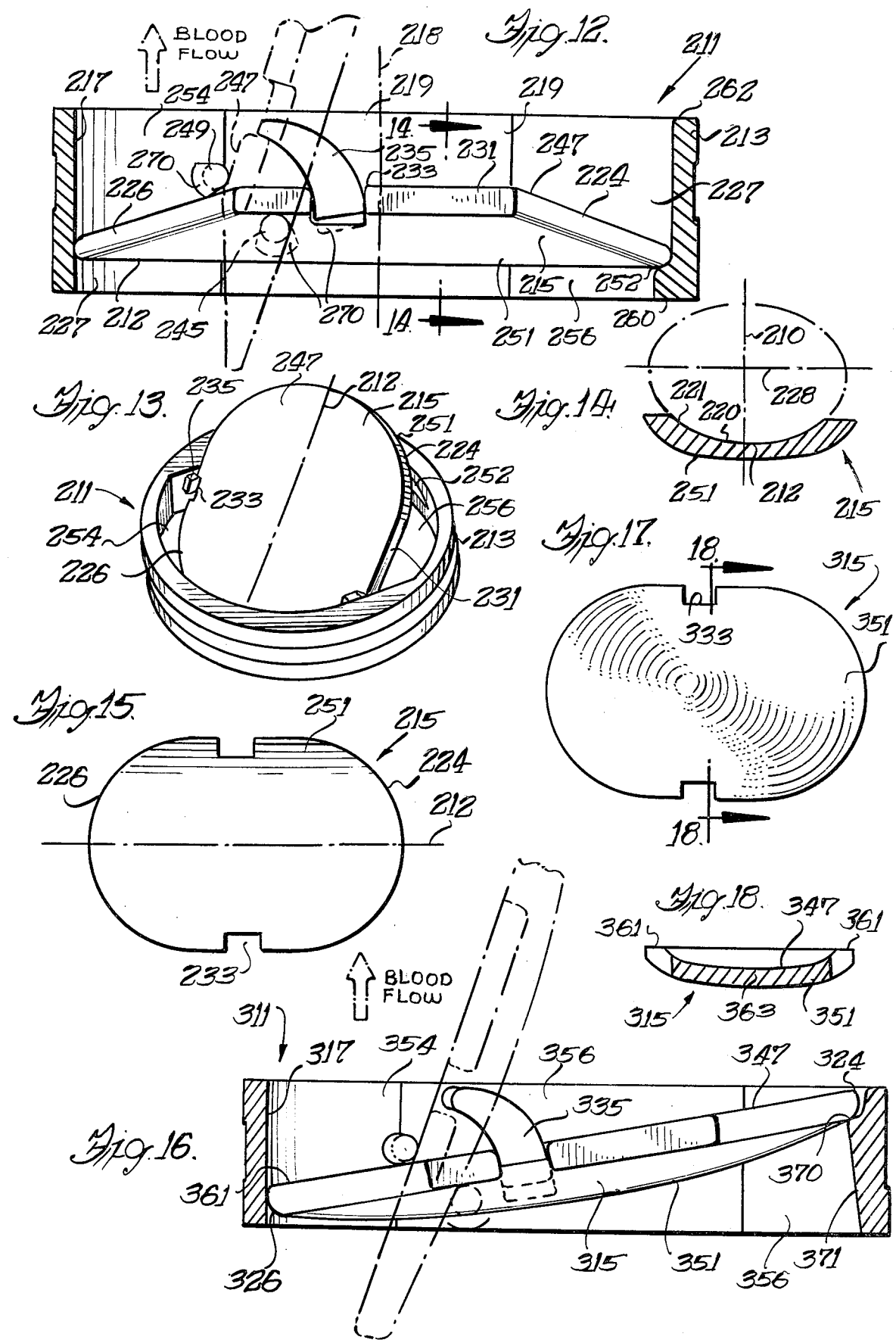

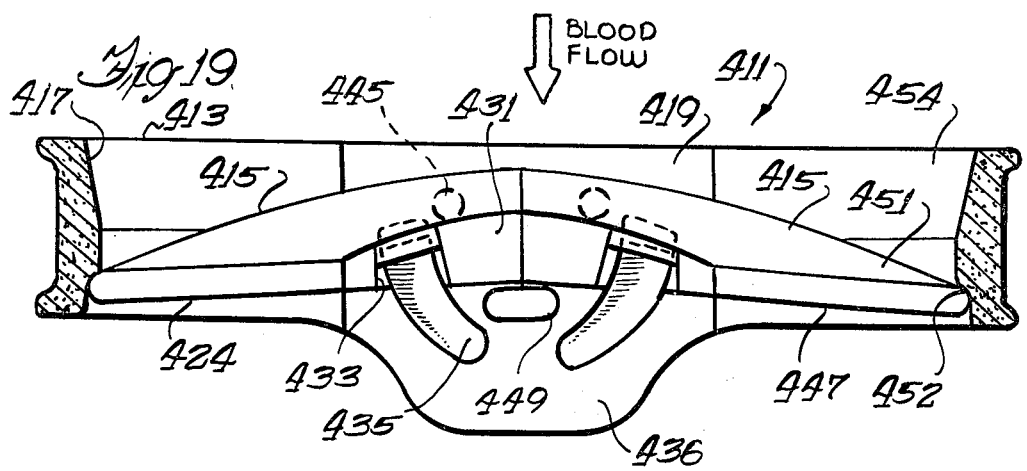
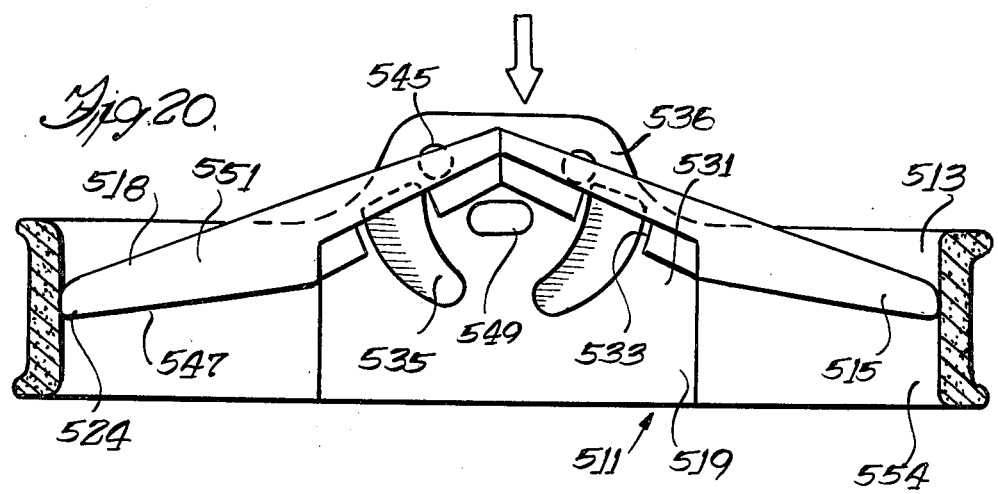
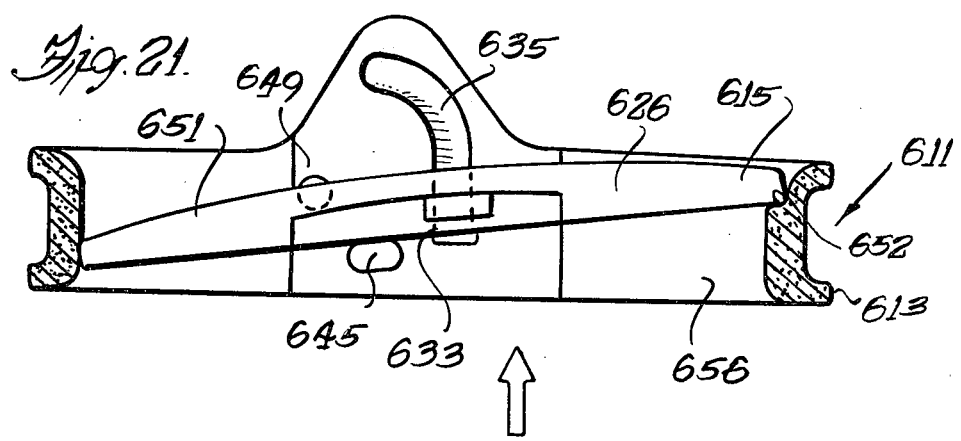

HEART VALVES HAVING EDGE-GUIDED OCCLUDERS

This application is a continuation in part of U.S. Patent application Ser. No. 200,910 filed Oct. 27, 1980, now abandoned.

This invention is related to heart valve prostheses and more particularly to heart valve prostheses using pivotal valve members.

BACKGROUND OF THE INVENTION

Various types of heart valve prostheses have been developed which operate hemodynamically as a result of the pumping action of the heart. Among the types of heart valves which have been developed are valves having single disc occluders which pivot along an eccentric axes to open and close the heart valves, such as that described in U.S. Pat. No. 3,825,957, and bileaflet heart valves, such as that described in U.S. Pat. No. 4,178,639. Although numerous designs have been proposed for heart valves, the need continues for improved heart valves which are intended for permanent implantation into the human heart.

In its open position, a valve should provide a passageway which is large and which has good flow characteristics so that blood flows freely therethrough with a minimum of drag and eddy currents. A heart valve should be responsive to blood flow to quickly open during the pumping stroke of the heart and snap back quickly when the heart relaxes to prevent regurgitation of the blood. The heart valve must, of course, be biocompatible and thromboresistant, and in this regard, it is important that all surfaces be well washed by blood to prevent stagnation which might lead to eventual clotting. The opening and closing of the valve should be sufficiently soft so as not to cause hemolysis (breaking of blood cells). The heart valve must withstand countless openings and closings, and particular care should be exercised so that the load-bearing surfaces, such as the pivot points and stops, do not wear out during the life of the patient. The above characteristics may be desirably achieved with a simple design which not only simplifies manufacture, but reduces the amount of obstacles to efficient blood flow, reduces the nooks and crannies where blood may stagnate and reduces the quality control problems associated with complexity.

The interengagement structures by which valve members are mounted in heart valve bodies frequently represent the regions where blood is most likely to clot and stagnate. Some designs of heart valves, e.g., U.S. Pat. No. 3,953,898, employ pins or shafts extending from the valve body into the valve member, and such an arrangement can easily lead to blood stagnation and clotting around the mounting members. Other heart valves, such as that described in U.S. Pat. No. 4,123,805, employ more exposed mounting members, yet unless the mounting members are in the direct flow of blood through the heart, the possibility remains that clotting around the mounting members will occur and adversely affect the operation of the heart valve.

SUMMARY OF THE INVENTION

The invention provides improved heart valve prostheses having valve members which may be either single disc occluders or pairs of leaflets. Notches formed in the periphery of the valve member extend entirely through the valve members from their upstream to their downstream surfaces and interengage with complementary projections which extend radially inward from the valve body to guide the notches in a curving pathway as the valve member swings between an open position to allow blood flow through the passageway and a closed position whereat the valve member blocks blood flow. The notches, which extend through the valve members from their upstream to their downstream faces, allow blood flow through the notches and around the projections so that blood does not stagnate and clot in the region of the valve member mountings. Protuberances associated with the projections cooperate therewith to define the pivotal axis, serve as open and closed position stops and retain the valve member within the valve body.

BRIEF DESCRIPTION OF THE DRAWINGS

FIG. 1 is a perspective view of a bileaflet heart valve embodying various features of the present invention shown in its open position;

FIG. 2 is a cross-sectional view, enlarged in size, of the heart valve taken along line 2—2 of FIG. 1;

FIG. 3 is a cross-sectional view similar to FIG. 2 illustrating the leaflets in the closed position;

FIG. 4 is a plan view of the heart valve of FIG. 1 shown in its closed position;

FIG. 5 is a cross-sectional view of the heart valve taken along line 5—5 of FIG. 2;

FIG. 6 is a perspective view of an alternative, embodiment of the present invention having a single disc occluder shown in its open position;

FIG. 7 is a plan view, enlarged in size, of the heart valve of FIG. 6 shown in its closed position;

FIG. 8 is a cross-sectional view of the heart valve taken along line 8—8 of FIG. 7;

FIG. 9 is a cross-sectional view, similar to that of FIG. 8, showing the partially closed occluder in ghost and the fully opened occluder in solid;

FIG. 10 is a cross-sectional view taken along line 10—10 of FIG. 8;

FIG. 11 is a fragmentary cross-sectional view taken along line 11—11 of FIG. 9;

FIG. 12 is an illustration of an alternative embodiment of a single occluder heart valve including a cross-sectional view of the valve body and an elevation view of the occluder within the valve body in its closed position in solid and in its open position in ghost;

FIG. 13 is a diminutive perspective view of the heart valve of FIG. 12 with the occluder in the fully open position;

FIG. 14 is a diminutive cross-sectional view of the occluder taken along line 14—14 of FIG. 12;

FIG. 15 is a plan view of the upstream side of the occluder;

FIG. 16 is a illustration of a further alternative embodiment of a single occluder heart valve including a cross-sectional view of the valve body and an elevation view of the occluder within the valve body in its closed position in solid and in its open position in ghost;

FIG. 17 is a diminutive plan view showing the upstream side of the occluder shown in FIG. 16;

FIG. 18 is a cross-sectional view taken along line 18—18 of FIG. 17;

FIG. 19 is an illustration of a further alternative embodiment of a bileaflet heart valve including a cross-sectional view of the valve body and an elevation view of the leaflets within the valve body in their closed position;

FIG. 20 is an illustration of a further alternative embodiment of a bileaflet heart valve including a cross-sectional view of the valve body and an elevation view of the leaflets within the valve body in their closed position;

FIG. 21 is an illustration of a further alternative embodiment of a single occluder heart valve including a cross-sectional view of the valve body and an elevation view of the occluder within the valve body in its closed position.

DETAILED DESCRIPTION OF THE PREFERRED EMBODIMENTS

Illustrated in FIG. 1 is a heart valve 11 which has an annular valve body or housing 13 which carries a pair of pivoting leaflets or valve members 15 which open and close to control the flow of blood through a central passageway 17 in the downward direction of the arrow 18 (FIG. 2). It should be understood that the heart valve 11 operates in any orientation and is not significantly affected by gravity; however, for ease of explanation, the valve is shown and described with its downstream side facing downward. The generally circular shape of the passageway 17 through the valve body 13 is altered slightly by a pair of diametrically opposite flat surfaces 19 and several inward protrusions hereinafter described.

The valve body 13 has a uniform height and is formed with a peripheral groove 23 about its exterior surface that accommodates a suturing ring (not shown) which may be any of the various types already well-known in the art. The suturing ring, of course, facilitates the sewing or suturing of the heart valve 11 to the heart tissue. The leaflets 15 are flat, and as best seen in FIG. 3, have a uniform thickness throughout. The leaflets 15 each have generally the shape of a half of a circular disc, having straight minor edges 25 which substantially meet in the closed position of the valve 11 and a major arcuate, generally semicircular edge 27 with a radius slightly less than the passageway radius to lie closely adjacent the interior wall 29 and substantially close off the passageway 17 in the closed position while leaving sufficient clearance between it and the interior wall to pivot freely. The semicircular edge of each leaflet 15 is interrupted on each side by parallal straight segments 31 at both ends of the leaflet disposed between the major and minor edges 25, 27. The straight segments 31 are spaced apart slightly less than the distance between the opposed flat surfaces 19 of the interior wall 29 and alternately serve as bearing surfaces as the leaflets 15 pivot between their open and closed positions. The cooperating flat bearing surfaces 19 of the interior wall 29 and straight segments 31 of the leaflets 15 assure the leaflets do not bind as they move away from the centerline during opening of the valve 11.

A pair of opposed notches 33, in the straight segments 31 of each leaflet 15 generally adjacent the minor edges 25 thereof, extend entirely through the leaflet from its upstream face 51 to its downstream face 47 and interengage with a pair of opposed projections 35 which extend inward from the corresponding flat segment 19 and are shaped to guide the notches in a generally arcuate or curving pathway which creates both pivotal and translational movement of the leaflet as it shifts between its open and closed positions. The depth of the notches 33 is slightly greater than the elevation of the projections 35 from the flat segments 19 so that the flat segments rather than the projections laterally position the leaflets 15 within the body 13. Each projection 35 has an upper end 37 which has horizontal dimensions substantially matched to the shape of the generally rectangular notches 33 to substantially fill the notches and prevent blood flow therethrough in the closed position of the valve 11. From its upper end 37, the transverse dimensions of each projection 35 decreases in the downstream direction toward a lower end 39 where a curved outer side 41 of the projection and a generally straight inner side 43 of the projection meet. The reduction in transverse dimension provides spacing between the notches 33 and the projections 35 so that blood will flow therebetween when the leaflets 15 are in their nonclosed positions and assure washing by the flowing blood of the surfaces defining the notches. The projections 35 have a slightly elongated configuration, generally in a direction between upstream and downstream, which results in the cooperating surfaces of the leaflets 15 and valve body 13 sliding against each other so that the surfaces are cleaned of blood which may otherwise tend to stagnate therearound. The projection length is substantially greater than the thickness of the leaflets at the region of each notch. The downward tanslation of the leaflets 15 outward of the valve body 13 also improves the blood flow through the passageway 17. It may be seen in FIG. 3 that, in the closed position, upstream bumps or protuberances 45 contact the leaflets 15 closely adjacent the notches 33 and, in the open position shown in FIG. 2, the upper protuberances contact the leaflets closely adjacent the straight minor edges 25.

The interengaging notches 33 and projections 35 are positioned close to the centerline of the valve body 13 so that the greater area of each leaflet 15 is distal to the centerline. For a heart valve 11 in the aortic location, as the respective ventricle contracts, the greater amount of force is exerted against the greater distal portion of each leaflet 15 causing the leaflet to swing in the downstream direction with its arcuate major edge 27 moving in a wide arc.

The upper protuberances 45 extending inward of the flat segments 19 are positioned just upstream and toward the center from each of the projections 35, and each provides a camming surface for the respective leaflet 15 as it swings between its open and closed positions. As each leaflet 15 swings open, its downstream face or surface 47 slides against an oval-shaped bump or protuberance 49 extending inward from each flat surface 19 that is positioned near the straight edge 43 of the projection 35. Thus during opening, a moving eccentric pivotal axis of each leaflet 15 is defined between its contact points with the oval protuberances 49. As seen in FIG. 2, each leaflet 15 becomes finally located between the corresponding upper protuberances 45 and the corresponding ends of the oval-shaped protuberances 49 to determine the open position of the leaflet 15 at an angle of about 10° to about 25° from the centerline.

At the end of the stroke, the respective ventricle relaxes to draw more blood into the chamber from the atrium, and the back flow of blood from the aorta exerts a drag upon the leaflets 15 that promptly swings each leaflet to its closed position. During closing, with the notches 33 guided by the projections 35, the upstream face or surface 51 of each leaflet 15 cams against the upstream protuberances 45 to define a movable eccentric pivotal axis between the contact points of each leaflet with the upstream protuberances. As best seen in FIG. 3, edge portions of the upstream surface 51 abut the upper protuberances 45 in the closed position, and a protuberance 55 supports the leaflet 15 at about the midpoint of its major arcuate edge 27. Each upper protuberance 45, which is located just upstream of the corresponding inward projection 35, is generally coplanar with the midpoint protuberances 55 so that the leaflets 15 in their closed position lie in a plane substantially perpendicular to the centerline of the circular passageway 17.

As the leaflets shift between thier open and closed positions, the notches, which are directly in the path of flowing blood, are continuously washed. The ends of the notches slide against the projections during opening and closing, one end mechanically contacting or scraping against the inner side 43 during opening and the other end scraping against the outer side 41 during closing. This sliding contact serves to continually scrape any blood which begins to stagnate around the notches or projections.

Variations may be made in the protuberances 55 which contact the major arcuate edges 27 of the leaflets 15. While the protuberances 55 are illustrated in FIG. 4 as small knobs, they may be elongated lip segments, if desired, to distribute the force of closing over a greater area. Alternatively, several spaced protuberances may be used to distribute the stresses.

The projections 35 and protuberances 49, 45 extending from the flat surfaces 19 of the interior wall 29 serve not only to guide and stop the leaflets 15 but also firmly hold the leaflets 15 in the heart valve body 13 and prevent their escape from either end of the projections. Throughout its swing from its open position, where each leaflet 15 is seated between the upper and oval protuberances 45, 49 and its closed position, where the leaflet seats against the upper protuberances, the arcuate path of movement of each leaflet is at all times defined by the interengagement of the projections 35 and the notches 33. In order to assemble the heart valve, it is necessary that the body 13 and/or the leaflets 15 be sufficiently resiliently deformable to be snapped into place so that the notches 33 interengage with the projections 35. The body 13 and leaflets 15, however, are sufficiently resistant to deformation that the leaflets are securely retained in the body and will not snap out during or subsequent to insertion into the heart.

Since the leaflets 15 in the closed position are in a plane perpendicular to the passageway centerline and since the upper and lower rims of the valve 11 are flat, the heart valve may be made with a very low profile. Such a low profile is desirable for good blood flow because it reduces drag in the most constricted region of blood flow and thereby reduce pressure loss through the heart valve.

The heart valve body 13 may be made of any suitably strong material which is biocompatible and thromboresistant or can be made so with suitable coatings. The body may be made of graphite, such as that sold under the trademark POCO and thereafter coated with pyrolytic carbon, such as that sold under the trademark PYROLITE. The leaflets may be formed entirely of pyrolytic carbon to provide thin responsive leaflets having sufficient strength and wear-resistance to withstand countless openings and closings. The leaflets may also be made of coated substrates.

Typically, a heart valve body 13 will have an outside diameter of about 27 mm. providing a passageway diameter of about 25 mm. and a height of about 5 mm. The arcuate edges of the leaflets 15 have a radius of 12 mm., and the straight side edge 31 of each leaflet is typically about 4 mm. long. Each is about 1 mm thick; the notches are about 1 mm. deep and 2.5 mm long. The projections and protuberances extend about 1 mm. into the passageway 17.

Illustrated in FIG. 6 is a single disc occluder embodiment of the invention in which a heart valve 111 having an annular valve body 113 carries a disc-shaped occluder 115 which hemodynamically opens and closes to control the flow of blood through a central passageway 117 in the direction of the arrow 118 (FIG. 8). The occluder 115 is mounted in the heart valve body 113 for shifting between an open and a closed position. For purposes of explanation, the single disc occluder 115 is shown and described with its downstream surface 147 facing upward.

Like the double leaflet valve 11, the single disc occluder valve 111 has a peripheral groove 123 that accommodates a suturing ring and a generally circular passageway 117 which is interrupted by diametrically opposite flat surfaces 119 and various projections and protuberances which guide or stop the occluder 115 as it opens and closes.

The occluder 115 is flat, having a uniform thickness throughout, as best seen in FIG. 8, and, as best seen in FIG. 7, has a circular periphery except for opposed straight edge segments 131 which lie closely adjacent flat surfaces 119 of the valve body 113 leaving an arcuate peripheral occluder edge 124 which extends downsteam when the valve 111 is open and an arcuate peripheral edge 126 which extends upstream when the valve is open. The straight edge segments 131 alternately abut one of the flat surfaces 119 of the interior wall 129 of the valve passageway 117 and serve as bearing surfaces for the occluder 115 as it opens and closes. A generally rectangular shaped notch 133 is formed in each straight segment 131 of the occluder 115 for interengagement with complementary elongated projections 135, which extend from the flat surfaces 119 into the passageway 117 and are proportioned to interfit within the notches 133. In the illustrated embodiment, the notches 133 are disposed slightly toward the downstream edge 124 (to the right side in reference to FIGS. 8 and 9). To provide for the upwardly elongated projections 135, opposed standards or supports 136 extend upward of the otherwise flat upper surface of the valve body 113. The supports 136, which extend in the downstream direction, provide for movement of the occluder outward of the valve body where it is less obstructing of flowing blood.

The projections 135 are shaped to guide the notches 133, which extend entirely through the occluder 115, in a generally arcuate pathway that creates both pivotal and translational motion of the occluder between its open and closed positions. The projections 135 have lower ends 137 (FIG. 9) which are proportioned to generally match the shape of and substantially fill the notches 133 to block blood flow therethrough in the closed position of the occluder 115. From the lower end 137 of each projection, an elongated section 140 extends downstream generally along the centerline and terminates in an upper end portion 139 that curves across the centerline plane, i.e., the plane through the centerline of the valve body 113 which is perpendicular to the flat surfaces 119. Downstream of the lower end 137, the projections 135 narrow in tranverse dimension and do not completely fill the notches whereby the surfaces of the notches 133 and projections 135 are well washed by flowing blood when the occluder 115 is in other than the closed position. The elongated shape of the projections results in sliding of the notches along the projections so that the surfaces of the notches are continuously scraped clean of accumulating blood.

As best seen in FIGS. 8 and 9, downstream protuberances 149 and upstream protuberances 145 extend outward from each of the flat surfaces 119 of the interior wall and provide surfaces against which the occluder 115 cams during opening. During opening, the movement of the occluder 115 is determined by the tracking of the notches 133 along the guiding projections 135 and the contact of the downstream face or surface 147 of the occluder with the downstream protruberances 149, and during closing, the movement of the occluder is determined by the tracking of the notches along the guiding projections and the contact of the upstream face or surface 151 of the occluder against the upstream protuberances 145. The upstream and downstream protuberances 145, are all disposed to one side of the centerline plane (to the left in reference to FIG. 8) and the upstream protuberances 145 generally define an eccentric axis along which the upstream surface 151 of the occluder 115 pivots during closing, and the downstream protuberances 145 generally define an eccentric axis along which the downstream surface 147 of the occluder pivots during opening. However, because the shape of the projections 135 is not arcuate, the occluder 115 cannot simply pivot against the protuberances 149, 145 but slides as well as pivots along the protuberances during opening and closing. During opening, the elongated shape of the projections 135 result in translational movement of the occluder 115 slightly downstream and outward of the valve body 113, and during closing, the occluder translates upstream. Hence the pivotal axis of the occluder 115 changes continuously during opening and closing. Because the upstream and downstream protuberances 145, 149 are all disposed to one side of the centerline plane, a greater portion of the occluder 115 is at all times to one side (to the right in reference to FIG. 8) of the changing eccentric pivotal axis and a lesser portion of the occluder will be to the other side of the axis.

The force differential which flowing blood exerts against the greater and lesser portions of the occluder 115 (relative to the changing pivotal axes) operates to move the occluder between its open and closed positions. For a valve 111 in the aortic position, when the ventricle contracts during the pumping stroke of the heart, the unequal force on the greater portion of the occluder 115 shifts the greater portion in the downstream direction so that the occluder pivots and cams against the downstream protuberences 149, and the notches 133 follow the path provided by cooperating projections 135.

When the respective ventricle relaxes drawing more blood from the atrium, the back pressure from the aorta tries to cause blood to flow downward or upstream through the valve, and the force of the flowing blood against the greater portion of the occluder 115 shifts it back to its closed position.

In addition to defining changing pivotal axes for the occluder, the upstream and the downstream protuberances 145, 149 serve to stop the occulder 115 in its open position, and the upstream protuberances 145 cooperate with auxiliary protuberances in the valve body 113 to stop the occluder 115 in its closed position. During opening, the entire occluder 115 is pushed against the downstream protuberances 149 and out of contact with the upstream protuberances 145. The occluder 115 shifts to open the passageway 117 with its downstream surface 147 in continuous contact with the downstream protuberance 149 until the upstream surface 151 of the occluder once again abuts the upstream protuberances 145 thereby stopping the occluder. The upstream and downstream protuberances 145, 149 are positioned relative to each other to stop the occluder 115 in its open position at an angle relative to the centerline plane of up to about 25°.

In the illustrated embodiment, the auxiliary protuberances, which cooperate with the upstream protuberances 145 to stop the occluder 115 in its closed position, include a pair of opposed protuberances 156 which extend from the flat surfaces 119 on the opposite side of the centerline plane from the upstream protuberances 145 and a protuberance 155 located at the midpoint of the arcuate valve body surface that is remote from the upstream protuberances. The occluder 115 stops in its closed position with its upstream surface 151 in contact with coplanar downstream surfaces of the upstream and auxiliary protuberances 145, 156, 155. In the illustrated embodiment, the upstream and auxiliary protuberances 145, 156, 155 are positioned to stop the occluder in its closed position in a plane along the upstream protuberances 145 perpendicular to the centerline plane; however, the protuberances might also be positioned to stop the occluder in the closed position angled up to about 25° from such a perpendicular plane with its downstream arcuate edge 124 pointing downstream. In valves where the occluder lies in the closed position other than in such a perpendicular plane, the shape of the occluder 115 is slightly elliptical in order that its arcuate edges lie closely adjacent the arcuate inner wall portions of the valve body 113. Other arrangements of protuberances may be used as well, such as elongated lips which distribute the stopping force of the occluder 115 over a wider area.

The interengagement of the notches 133 with the guiding projections 135 in cooperation with the several protuberances also serves to maintain the occluder 115 within the valve body 113. Translational movement of the occluder 115 is at all times narrowly defined by the interengagement of the notches 133 and the projections 135, preventing the occluder from sliding out of the valve body 113. The shift to the open position is stopped by the upstream and downstream protuberances 145, 149 before the notches 133 pass beyond the downstream ends of the projections 135, and the shift to the closed position is stopped by the upstream and auxiliary protuberances 149, 156, 155 before the notches pass beyond the upstream ends of the projections.

The proportions of the single disc occluder valve 111 correspond generally to the proportions of the two leaflet valve 11. The upstanding supports 136 may extend about 5 mm past the downstream edge of the valve body 113 to allow substential downstream translation of the occluder 115. Since the upwardly extending supports 136 extend from only a small portion of the valve body 113, they do not provide any significant circumferential restriction to blood flow.

Illustrated in FIG. 12 is an alternative embodiment of a single occluder heart valve 211 in which the occluder 215 has an arcuate cross section and a generally uniform thickness. The occluder 215 has a configuration generally that of a portion of a tube, such as a hollow right circular or elliptical cylinder. The preferred occluder configuration is generally a portion of a hollow, right, elliptical cylinder with the minor elliptical axis 210 (FIG. 14) intersecting the centerline 212 of the occluder (FIG. 13), and the occluder is disposed in the valve body 213 with its convex surface 251 facing upstream. The elliptical cross-sectional configuration provides a region 220 along its centerline 212 which is fairly flat relative to the edge regions 221 as best seen in FIG. 14. The length of major elliptical axis 228 of the occluder is preferably between about 120% and about 200% of the passageway diameter, and the minor elliptical axis 210 is between about 50% and about 170% of the passageway diameter. The depth X (FIG. 14) of the concave surface, as measured from the occluder centerline to its base, is between about 15 to about 30 percent of the passageway diameter.

The occluder 215 may be orientated within the valve body 213 so that it seats in its closed position with its straight centerline 212 either in a plane perpendicular to the passageway centerline 218 or angled therefrom up to about 25° with its downstream arcuate edge 224 pointing downstream. The downstream arcuate edge 224 and upstream arcuate edge 226 have the general shape of the intersection between the right cylinder that defines the shape of the occluder 215 and the right circular cylinder that defines the interior wall 227 of the valve passageway 217.

The occluder 215 is formed with flat lateral edge segments 231 which lie closely adjacent to diametrically opposite flat surfaces 219 on the interior wall of the valve body and which alternately bear against the flat surfaces as the occluder shifts slightly laterally. Guiding projections 235 and upstream and downstream protuberances 245, 249 extend generally radially inward from the interior wall of the valve body, and a generally rectangular shaped notch 233 is formed adjacent each flat segment 231 extending completely through the occluder for interengagement with the opposed projections 235.

The action of the occluder 215 is similar to the action of occluder 115 of the heart valve 111, described hereabove in reference to FIGS. 6–11. The notched occluder 215 is guided for pivotal and translational movement during opening and closing by the elongated projections 235. The occluder stops in its closed position with its upstream surface 251 abutting upstream protuberances 245 and an auxiliary lip 252 (FIG. 12) which projects inward on the arcuate interior wall, being located on the side of the centerline 218 remote from the upstream protuberances. The lip 252 may extend either partially or fully around the interior wall between the flat surfaces 219. The occluder 215 stops in its open position with its downstream surface 247 abutting downstream protuberances 249 and with its upstream surface 251 in contact with the upstream protuberance 245, wherein its centerline 212 forms an angle of from about 10° to about 25° with the passageway centerline 218.

When the occluder is in the open position, it defines a minor passageway portion 254 along its concave surface 247 (to the left in FIG. 12) and a major portion 256 along its convex surface 251. The convex surface 251 of the occluder 215 projects into the major passageway portion 256 while the concave surface 247 enlarges the minor passageway 254 portion. Thus the arcuate cross section of the occluder 215 tends to somewhat equalize the passageway portions 254, 256. In tending to equalize the passageway portion 254, 256, the occluder assures that the area of the minor passageway portion will not overly restrict the free flow of blood to such an extent that little flow will take place, and thus increases the performance of the valve 211. Shaping the occluder 215 to tend to equalize the size of the passageway portions 254, 256 allows the upstream and downstream protuberances 245, 249 to be located further from the centerline 218 than for a valve having equal blood flow performance which uses a flat occluder. As a result, a greater force differential is exerted by back flowing blood which acts to quickly close the valve 211. As seen in FIG. 12, the upstream and downstream protuberances 245, 249 are disposed close to the edges of the flat segments, and they and the guiding projections 235 are disposed all on one side of the centerline.

As a means of reducing sharp cavities where blood may tend to stagnate and coagulate and for streamling flow, non-bearing surfaces 270 of the projections 235 and protuberances 245, 249 are blended into the surfaces of the interior wall of the passageway 217.

Illustrated in FIG. 16 is a further alternative embodiment of a single occluder heart valve 311. The occluder 315 is dome-shaped having a convex-concave configuration generally that of a sector of a hollow sphere with the convex surface 351 facing upstream in the closed position of the heart valve. As seen in FIG. 18, the dome-shaped occluder 315 preferably has a generally uniform thickness. The valve body 313 resembles the body 213 of the heart valve 211 described in reference to FIGS. 12–15 with appropriate adjustments in positioning of the protuberances 345, 349 and projections 335 as required by the configuration of the occluder 315. The arcuate edges 324, 326 of the occluder 315 are in the shape of segments of either circles or ellipses, depending on whether the occluder 315 seats in the closed position with its base 361 in a plane perpendicular to the passageway centerline or, as shown, at an angle from such a perpendicular plane up to about 20°. The occluder 315 seats in its closed position with its downstream arcuate edge 324 abutting a lip 370 formed in the interior wall 371 of the valve body 313 at a location remote from the projections 335.

In its open position, the occluder 315 defines a minor passageway portion 354 along its downstream surface 347 and a major passageway portion 356 along its upstream surface 351. The convex upstream surface projects into the major passageway portion, and the concave downstream surface 347 expands the minor passageway portion 354 tending to somewhat equalize blood flow along both sides of the occluder. To this end, it is preferred that the depth Y (FIG. 18) of the dome, as measured from its base 361 to the apex 363 of its concave surface 347, be about 15 to about 30 percent of the passageway diameter.

Illustrated in FIG. 19 is a further alternative embodiment of a bileaflet heart valve 411 in which each of the leaflets 415 has a convex-concave configuration generally that of one-half of a sector of a hollow sphere. The convex surface 451 of each of the leaflets faces upstream, and the leaflets in their open position provide a generally circular central region between their concave downstream surfaces 447 with good blood flow characteristics.

Projections 435 extending from diametrically opposite flat regions 419 of the valve body 413 project generally radially inward and interenagage with notches 433 extending from the upstream to the downstream surfaces adjacent flat peripheral segments 431 of the leaflets to guide the leaflets on curving pathways as they shift between their open and closed positions. The projections 435 extend partially into diametrically opposite upstanding standards 436 which project downstream of the heart valve body 413, and when the leaflets shift downstream of their open position, they move outwardly of the orifice region of greatest restriction of the heart valve body thereby improving the blood flow performance.

Each of the leaflets 415 is stopped in its open position with its convex upstream surface 451 in contact with a pair of opposed upstream protuberances 445 associated with the corresponding guiding projections 435 and with its downstream surface 447 in contact with a pair of diametrically opposed downstream protuberances 449 disposed centrally between the projections on each side of the heart valve. Each of the leaflets is stopped in its closed position with its upstream convex surface 451 in contact with the upstream protuberances 445 and with its major peripheral edge 424 in contact with a ledge or lip 452 extending around the interior wall 454 of the valve body. Each of the leaflets is stopped in its open position with its major peripheral edge 424 in a plane which meets the centerline at an angle of between about 10° and about 25°, and each of the leaflets is stopped in its closed position with its major peripheral edge 424 in a plane which meets with the centerline of the valve body at an angle of between about 65° and about 90°. When, as illustrated, the leaflets 415 seat in their closed position angled slightly from a plane perpendicular to the centerline, the major peripheral edge 424 of each is formed with a slightly elliptical shape, as defined by the intersection of the plane of the peripheral edge and the generally cylindrical interior surface of the valve body.

Illustrated in FIG. 20 is a further alternative embodiment of a bileaflet heart valve 511 in which each of the leaflets 515 has a convex-concave configuration generally that of a sector of a hollow right cylindrical tube. The leaflets 515 have flat edge sections 531 in which notches 533 are formed on opposite sides of the leaflet centerlines 518. The notches interengage with projections 535 extending from opposite flat portions 519 of the interior of the valve body. The projections 535 guide the leaflets in shifting between their open and closed positions and extend partially into upstanding standards 536 which project from the upstream side of the valve body 513.

The leaflets 515 are stopped in the open position with their convex upstream surfaces 551 in contact with upstream protuberances 545 associated with the corresponding projections 535 and their downstream surfaces 547 in contact with opposed downstream protuberances 549 disposed centrally between the projections on each of the flat portions 519. In their closed position, the leaflets are stopped with their upstream surfaces 551 in contact with the upstream protuberances 545 and with their major peripheral edges 524 in contact with the interior arcuate wall 554 of the valve body.

The convex-concave configuration of the leaflets 515 provides a generally elliptical central passageway with good blood flow characteristics past the facing concave surfaces 547 of the leaflets in their open position. The standards 526, which project in the upstream direction, permit the leaflets to seat in their closed position with their major edges 524 still pointing fairly sharply downstream. For leaflets which seat in their closed position at a sharp angle relative to the valve body, auxiliary protuberences or lips can be optionally omitted because their major edges 524 bear against the arcuate interior wall. Preferably the leaflets, in heart valves having standards extending upstream, seat in their closed position with their centerline 518 meeting the centerline of the valve body at an angle of between about 65° and about 70°. Because in their open position, the centerlines of the leaflets meet the centerline of the valve body at an angle of between about 10° and about 25°, the distance the leaflets are required to shift between their open and closed positions is thereby small, i.e., only between about 45° and about 60°. The small shifting movement of the leaflets required to close the valve 511 hastens closing and reduces backflow through the valve.

Illustrated in FIG. 21 is a further alternative embodiment of a heart valve 611 having a single occluder 615 that has a concave-convex configuration generally that of a sector of a hollow sphere with its concave surface 651 facing upstream. The interengagement of peripheral notches 633 with inwardly extending elongated projections 635 serves to guide the occluder in shifting between its open and closed positions. The occluder 615 is stopped in its open position in contact with upstream and downstream protuberances 649, 645. In its closed position, the occluder contacts the upstream protuberances 649, and its downstream peripheral edge 626 seats along a lip 652 which extends radially inward from the interior wall 656 of the valve body 613 at a location remote from the upstream and downstream protuberances. In the closed position, the illustrated occluder 615 seats in the valve body 613 with the plane of its periphery offset at an acute angle from a plane perpendicular to the centerline of the valve passageway.

Many advantages of the illustrated heart valves should now be more fully appreciated. The low profile of the heart valves, the large generally unobstructed passageway, and the translation of the valve members outward of the valve body in the open position contribute to excellent flow of blood therethrough. Almost all surfaces are fully exposed to flowing blood which washes the surfaces and prevents stagnation and clotting. The diminishing transverse dimensions of the projections permit flowing blood to wash the most restricted area, i.e., between the notches and the projections, and in this regard, the configuration of the projections which results in translational movement of the valve member also causes some sliding of the notch surfaces along the projection surfaces to continually clean these surfaces. Since the swinging valve members are generally in contact with the valve body at at least one set of protuberances as well as along the projections, and since the contact points are continually changing, the pressures between the valve members and the bodies are well distributed and wear on the heart valves is minimized. Similarly, the distribution of the opening and closing forces over several surfaces cushions the impact so that no significant hemolysis occurs. The design of the heart valves is simple so that they may be easily manufactured and reproduced according to exacting standards to provide lifelong trouble-free use.

While the invention has been described in terms of certain preferred embodiments, modifications obvious to one of the ordinary skill in the art may be made without departing from the scope of the invention. For example, the notches may have an arcuate rather than a rectangular shape, and the projections would have a correspondingly rounded transverse configuration.

A number of embodiments have been shown and described which are well representative of edge guided heart valves of the present invention. These embodiments incorporate a variety of features which are incorporated according to the requirements of the patient and manufacturing considerations into a variety of modifications or permutations. It will be understood that the various permutations, which arise from rearranging the various features that have been described herein in reference to the illustrated embodiments, are within the scope of the invention.

Various features of the invention are set forth in the following claims.

What is claimed is:

1. A heart valve prosthesis for allowing blood flow therethrough in a specific direction including
    a generally annular valve body having an interior surface defining a central passageway for blood flow therethrough,
    occluder means for blocking the flow of blood through said passageway, said occluder means having an upstream face and a downstream face,
    notches extending through said occluder means between said upstream face and said downstream face and being formed in opposite locations in the periphery of said occluder means,
    complementary projections which are elongated generally in a direction between upstream and downstream and of a length substantially greater than the thickness of said occluder means at said notch, which extend generally radially inward from said interior surface into said passageway and which are proportioned to interfit within said notches, said projections being exposed to free flow of blood and having opposite elongated surfaces that are alternately mechanically contacted by edges of said notches during alternate opening and closing movement, the shape of said projections being such to guide said occluder means along a path during shifting between open and closed positions that creates both pivotal and translational movement,
    first means in said annular valve body for engaging said upstream face of said occluder means and providing a stop in the closed position, and
    second means in said annular valve body for engaging said downstream face of said occluder means and providing a stop in the open position.

2. A heart valve in accordance with claim 1 wherein said projections extend from substantially flat surfaces formed at diametrically opposite locations in the interior surface of said valve body, and said notches are located in straight segments of said periphery of said occluder means.

3. A heart valve in accordance with claim 1 wherein said projections have end sections which substantially fit said notches when said occluder means is stopped in said closed position and said projections decrease in transverse dimension in the direction which said notches travel as said occluder means shifts to said open position to assure washing by the flowing bloodstream of the surfaces defining said notches.

4. A heart valve in accordance with claim 1 wherein said valve body has a substantially uniform height.

5. A heart valve in accordance with claim 1 wherein said valve body has a pair of opposed upstanding standards into which portions of said projections extend.

6. A heart valve in accordance with claim 5 wherein said standards extend from said valve body in the upstream direction.

7. A heart valve in accordance with claim 5 wherein said standards extend from said valve body in the downstream direction.

8. A heart valve in accordance with claim 1 wherein said occluder means has a convex-concave configuration with said upstream face being convex.

9. A heart valve in accordance with claim 1 wherein said occluder means has a concave-convex configuration with said upstream face being concave.

10. A heart valve according to claim 1 having occluder means in the general shape of a sector of a hollow sphere.

11. A heart valve in accordance with claim 1 wherein said upstream face and said downstream face are flat.

12. A heart valve according to claim 1 wherein said occluder means comprises a pair of leaflets each having a curved major edge, a minor edge which lies closely adjacent the minor edge of the other of said leaflets in said closed position and a pair of said notches formed in opposed locations in its periphery.

13. A heart valve according to claim 12 wherein said first means stops said leaflets in said closed position with said major edges lying in planes which meet the centerline of said valve body at angles of between about 65° and about 90°.

14. A heart valve according to claim 12 wherein said heart valve body has a pair of protuberances at diametrically opposite locations to contact said leaflets at about the midpoints of said major edges in said closed position.

15. A heart valve in accordance with claim 12 wherein each of said leaflets is generally a section of a tube of curved cross section, each of said leaflets having a generally straight centerline with said notches formed on opposite sides of said centerline.

16. A heart valve in accordance with claim 15 wherein said first means stops said leaflets in said closed position with said centerlines of said leaflets meeting the centerline of said valve body at angles of between about 65° and about 90°.

17. A heart valve in accordance with claim 1 wherein said occluder means comprises a unitary occluder.

18. A heart valve in accordance with claim 17 wherein said occluder means has a peripheral edge and said first means stops said occluder in said closed position with said peripheral edge in a plane which meets the centerline of said valve body at an angle of between about 65° and about 90°.

19. A heart valve in accordance with claim 1 wherein said second means stops said occluder means in said open position with said upstream face abutting said first means.

20. A heart valve phosthesis for allowing blood flow therethrough in a specific direction including
    a generally annular valve body having an interior surface defining a central passageway for blood flow therethrough,
    a single occluder having a downstream face and an upstream face,
    a pair of notches formed in opposite locations in the periphery of said occluder and extending through said occluder between said upstream face and said downstream face,
    a pair of complementary projections which are generally elongated in a direction between upstream and downstream and of a length substantially greater than the thickness of said occluder at said notch, which extend from said interior surface into said passageway and which are proportioned to interfit within said notches for guiding said occluder in pivoting action between open and closed positions, the shape of said projections being such to guide said occluder along a curved path during shifting between said open and closed positions that creates both pivotal and translational movement, the dimension of said notches being such that said occluder is unrestrained from escaping past either end of said elongated projections, first protruding bump means formed in said annular valve body for engaging said upstream face of said occluder and providing a stop in the closed position, and second protruding bump means in said annular valve body for engaging said downstream face of said occluder and providing a stop in the open position, said first and second bump means cooperating with said elongated projections to prevent the escape of the occluder therefrom.

21. A heart valve in accordance with claim 20 wherein said occluder is generally a section of a tube of curved cross section, said occluder having a generally straight centerline with said notches formed on opposite sides of said centerline.

22. A heart valve according to claim 21 wherein said occluder is generally a section of a tube in the shape of a hollow right elliptical cylinder with its downstream face being concave, the length of the major elliptical axis being between about 120 and about 200 percent of the diameter of said passageway and the length of the minor elliptical axis being between about 50 and about 170 percent of the length of the diameter of said passageway.

23. A heart valve in accordance to claim 22 wherein the depth of said concave face is between about 15 and about 30 percent of the diameter of said passageway.

24. A heart valve in accordance with claim 20 wherein said occluder is dome-shaped with its downstream face being concave.

25. A heart valve in accordance with claim 24 wherein the height of said dome, from its base to the apex of said concave face, is between about 15 and about 30 percent of the diameter of said passageway.

* * * * *